United States Patent [19]

Fry et al.

[11] Patent Number: 5,018,508

[45] Date of Patent: May 28, 1991

[54] SYSTEM AND METHOD USING CHEMICALS AND ULTRASOUND OR ULTRASOUND ALONE TO REPLACE MORE CONVENTIONAL SURGERY

[76] Inventors: Francis J. Fry, General Delivery, St. James, Beaver Island, Mich. 49782; Steven L. Griffith, 7461 N. Dorothy Dr., Indianapolis, Ind. 46220

[21] Appl. No.: 493,442

[22] Filed: Mar. 14, 1990

Related U.S. Application Data

[63] Continuation-in-part of Ser. No. 202,015, Jun. 3, 1988, abandoned.

[51] Int. Cl.$^5$ .............................................. A61B 17/00
[52] U.S. Cl. ................................. 128/24 AA; 604/28; 604/48
[58] Field of Search .................... 128/24 A, 660.03; 604/22, 28, 48

[56] References Cited

U.S. PATENT DOCUMENTS

| | | | |
|---|---|---|---|
| 4,655,744 | 4/1987 | Thistle et al. | 604/28 |
| 4,696,668 | 9/1987 | Wilcox | 128/24 A |
| 4,723,941 | 2/1988 | Thistle et al. | 604/152 |
| 4,755,167 | 7/1988 | Thistle et al. | 604/28 |
| 4,758,596 | 7/1988 | Thistle et al. | 604/48 |

Primary Examiner—Lee S. Cohen
Assistant Examiner—John D. Zele
Attorney, Agent, or Firm—Barnes & Thornburg

[57] ABSTRACT

A method for rendering a gallbladder dysfunctional without surgical removal comprises the steps of infusing the gallbladder with methyl-tert-butyl ether (MTBE), then, while the gallbladder is so infused, irradiating the gallbladder with an ultrasound beam in such an ultrasound delivery format as not to elevate the average temperature of the gallbladder more than five degrees Centigrade over the period of treatment, and then removing the MTBE from the gallbladder.

4 Claims, 2 Drawing Sheets

SYSTEM AND METHOD USING CHEMICALS AND ULTRASOUND OR ULTRASOUND ALONE TO REPLACE MORE CONVENTIONAL SURGERY

This is a continuation-in-part of U.S. application Ser. No. 202,015, filed June 3, 1988, now abandoned.

BACKGROUND OF THE INVENTION

Conventional surgery relies on opening the overlying skin and other tissues to expose the diseased organ or tissue which is then excised or repaired. The body regions and overlying tissues are subsequently closed. One typical conventional surgery procedure, cholecystectomy, generally includes removal of the gallbladder with contained gallstones. Cholecystectomies also are performed on diseased gallbladders when gallstones are not present. Another conventional surgical procedure is the appendectomy, which may be performed once acute inflammation of the appendix is checked. This, of course, prevents future inflammation, since the appendix is physically removed.

It is known to impair organ function to mimic a disease's effect on organ function using ultrasound. See U.S. Pat. No. 4,216,766. Combined ultrasound/chemotherapy treatment of cancerous tumors is also known. See U.S. Pat. No. 4,556,070.

SUMMARY OF THE INVENTION

An object of the present invention is to eliminate certain conventional surgeries. In the case of the gallbladder, for such an object to be achieved, it is necessary that the gallbladder can be made to disappear as a result of the inventive non-invasive or minimally invasive treatment. For other disease situations a similar result must be achieved.

It has been demonstrated that the combination of solvents and ultrasound can eliminate gallstones and other calculi occurring in the body by dissolution. It is an object of the present invention to expand that known treatment regime to include the elimination of gallstones by exposure to ultrasound in a non-shock wave generating delivery format. It is an object of the present invention to expand that known treatment regime to include the elimination of the gallbladder itself in addition to elimination of gallstones using chemicals and ultrasound. Although the present disclosure is made in the context of removal of the gallbladder, no intention is to be imputed or inferred to exclude any other organ or tissue. Nor is any exclusion implied for those organs or tissues in which the method can be applied intraoperatively. This includes, but is not limited to, ductile systems such as the cardiovascular system, in which either externally applied or intraductally applied ultrasound is used in combination with appropriate chemical species.

The system according to one aspect of the invention involves an appropriate delivery mechanism, such as a delivery needle or catheter, to deliver the appropriate chemicals to the desired site. Any number of schemes including diagnostic ultrasound may be used if needed to identify the desired site and to direct the delivery vehicle to the site. In some cases the appropriate chemical species may be delivered systemically by various methods (e.g. percutaneously, transdermally, orally). Once the chemicals are present at the treatment site in the correct concentrations and chemical configurations, the site is irradiated by an appropriately shaped ultrasound beam for treatment.

According to one aspect of the invention, a method for rendering a gallbladder nonfunctional without surgical removal comprises the steps of infusing the gallbladder with methyl tert-butyl ether (MTBE) and irradiating the gallbladder with an ultrasound beam in such a format as not to elevate the average temperature of the gallbladder more than five degrees Centigrade over the period of treatment.

Illustratively according to this aspect of the invention, the step of infusing the gallbladder with MTBE comprises the steps of placing a catheter into the gallbladder, periodically administering MTBE bolus into the gallbladder, and removing the MTBE from the gallbladder.

The step of irradiating the gallbladder with an ultrasound beam comprises the step of irradiating the gallbladder while it contains MTBE.

Further illustratively according to this aspect of the invention, the method further comprises the step of flushing the gallbladder with a sterile fluid after the step of removing the MTBE from the gallbladder.

Additionally according to this aspect of the invention the ultrasound delivery format includes a frequency in the range of 200-250 KHz, a spatial peak-temporal peak (SPTP) intensity of 6-24 W/cm$^2$ over the cross sectional area at the gallbladder, a duty cycle in the range of 10%-50%, and an ultrasound exposure time of 30-180 minutes.

According to another aspect of the invention, a method of reducing a gallstone in the gallbladder consists essentially of the step of subjecting the stone to ultrasound irradiation in such a delivery format as not to elevate the average temperature of the gallbladder more than five degrees Centigrade over the period of treatment and so as not to irradiate the gallbladder with shock waves. For example, starting with a base temperature of 36° C., which is readily induced in the human body, being essentially only 1° C. below normal body temperature of 37° C., this temperature rise would be to at most 41° C., which is below the hyperthermia range.

According to yet another aspect of the invention, a method of reducing a gallstone in the gallbladder consists essentially of the step of subjecting the stone to ultrasound irradiation in such a delivery format as not to elevate the average temperature of the gallbladder more than five degrees Centigrade over the period of treatment.

According to a further aspect of the invention, a method of reducing a gallstone in the gallbladder consists essentially of the step of subjecting the stone to ultrasound irradiation in such a delivery format as not to irradiate the gallbladder with shock waves.

DESCRIPTION OF THE DRAWINGS

The invention may best be understood by referring to the following description and accompanying drawings which illustrate the invention. In the drawings.

DETAILED DESCRIPTION OF THE INVENTION

Figure 1:
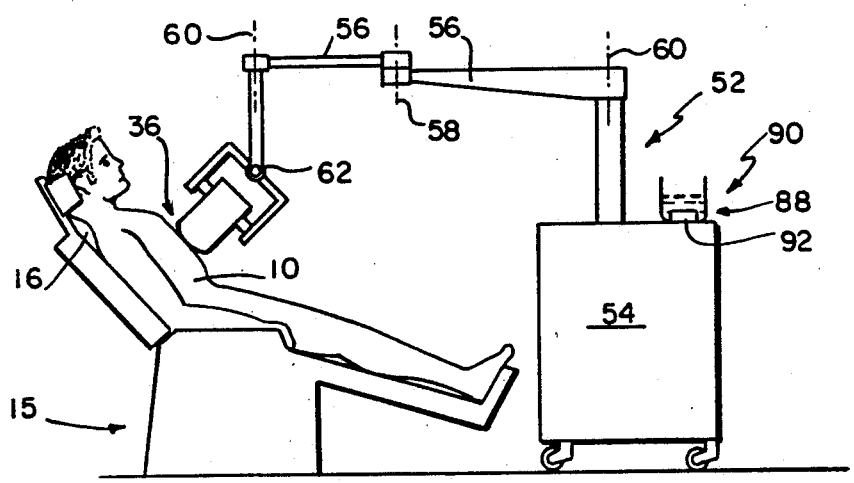
FIG. 1 illustrates a side elevational view of an apparatus for conducting the methods of the present invention.

The system of FIG. 1 illustrates a configuration for transcutaneous application of broad-beam ultrasound directed to the gallbladder. In this embodiment, a chemical species is supplied by a small (4 French) indwelling catheter in the gallbladder. This catheter is inserted transcutaneously and transhepatically using, for example, the catheter Sacks ONE-STEP fluid-drain kit, Catalog No. 11-KSD5 5.5 F available from Electro-Catheter Corp., Rahway, N.J., 07065. In the embodiment of FIG. 1, a patient 10 reclines on a table 15. Table 15 has a back-mounted sound absorbing system 16 to absorb ultrasound passing through the patient 10 and exiting through the patient's back. The patient's gallbladder 20 has indwelling catheter 23 for insertion and, if necessary, withdrawal, of the appropriate chemical(s). A thin, acoustically transparent diaphragm 29 is in contact with patient 10 through a conventional acoustic coupling medium, such as a coupling gel. The transducer treatment head 36 is manually guided over the gallbladder, using, in this embodiment, real-time ultrasonic guidance provided by a diagnostic transducer system 38 which is lowered into a position 40 near diaphragm 29 by a suitable type of actuating mechanism (not shown). In this down position 40, the gallbladder 20 and any gallstones 46 can be clearly visualized. Diagnostic transducer 38 and therapy transducer 48 (illustrated in a position withdrawn sideways by means of a suitable type of actuator (not shown)) are coaxially aligned so that once the treatment site is visualized, the therapy beam from therapy transducer 48 can be readily positioned to be appropriately aimed at the visualized site.

Figure 2:
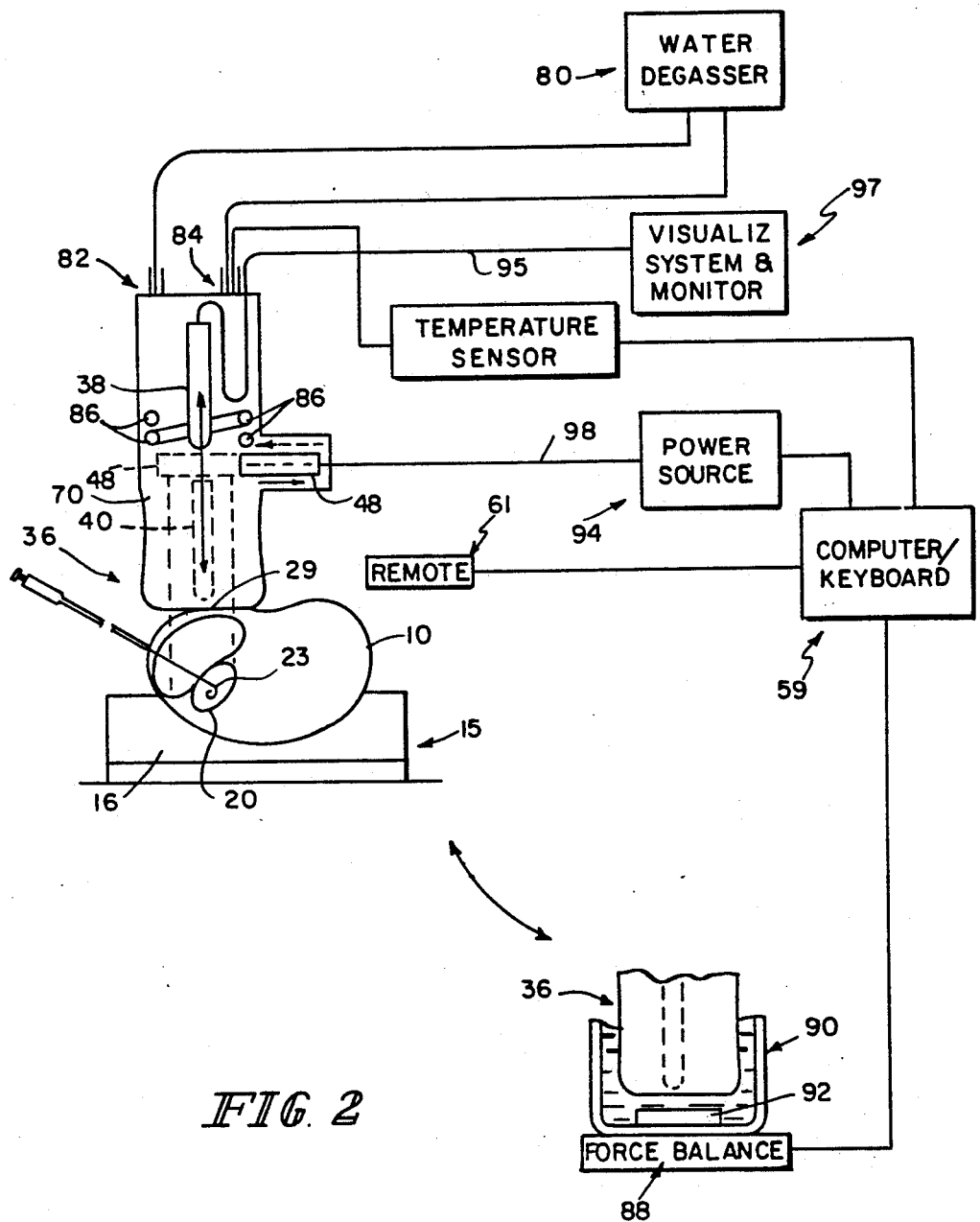
FIG. 2 illustrates a highly, and partly block, diagrammatic sectional side elevational view of part of an apparatus for conducting the methods of the present invention.

Manual guidance of treatment head 36 is implemented by an electrical lift system 52 mounted in a base 54 and having arms 56 with articulated locking points 58. Two additional degrees of motion are provided at points 60 and 62. These points are also locked after final positioning. In this configuration, the ultrasound beam provided by therapy transducer 48 is broad at the treatment site, as indicated by broken lines in FIG. 2, so no substantial movement of the target outside of the therapy beam is experienced during routine breathing of the patient. Transducer 38 can also be positioned to inspect the diaphragm 29 acoustically at the skin-contact area to determine if any air is trapped in the coupling gel layer. Once transducer 38 is withdrawn, therapy transducer 48 is moved laterally into the broken line position illustrated in FIG. 2 by its actuating mechanism. The actuating mechanisms for transducers 38 and 48 are controlled by a computer/keyboard 59, or by a direct keyboard interface or remote button 61.

Head 36 is filled with degassed water 70 to couple the ultrasound beams to diaphragm 29. A water degasser 80 provides water 70 to head 36 through inlet and outlet 82, 84, respectively. Water 70 is maintained at approximately room temperature by cooling coils 86 through which water circulates from a heat exchanger (not shown) in base 54. Head 36 is designed to act as a wave guide providing a broad beam of collimated ultrasound beyond diaphragm 29. The particular embodiment of the present invention employs an undulating internal wall configuration to suppress in-phase wave patterns which otherwise would tend to result in focussing of the ultrasound beam outside of diaphragm 29.

The total acoustic power output of therapy transducer 48 is monitored before patient treatment is begun, using a radiation force balance 88 which is coupled to computer/keyboard 59. Transducer treatment head 36 is immersed in a degassed water-filled chamber 90 having sound absorbing material 92 at its base. This calibration is performed while the therapy transducer 48 is driven in a pulsed format to eliminate standing waves in chamber 90. Computer/keyboard 59 controls a number of voltage settings on therapy transducer 48 through a power source 94 for this calibration. The total radiated force is read by force balance 88 and transmitted to computer/keyboard 59. If the system is outside predetermined error limits of desired radiation force, the system is locked out and will not operate. The actuating mechanisms for transducers 38 and 48 also have position encoders so that computer/keyboard 59 can monitor the spatial locations of transducers 38 and 48. Radiation force balance 88 is mounted on base 54 for convenience.

Electrical lead 95 couples transducer 38 with a visualization system and monitor 97. Electrical lead 98 couples therapy transducer 48 with power source 94. Power source 94 is a wide-band power amplifier (0 to 1000 watts output; 200 KHz to 5 MHz frequency range) which is driven by a selectable frequency source and a gate, both controlled by computer/keyboard 59. A feedback control loop is associated with the power amplifier which maintains the output power to therapy transducer 48 even though there may be minor changes in the electrical impedance of therapy transducer 48 due to patient breathing and the like.

All pertinent patient data is entered through the computer/keyboard 59 and appears on the monitor of computer/keyboard 59. All appropriate ultrasound delivery parameters are also entered into computer/keyboard 59. Once the treatment starts, computer/keyboard 59 controls all functions automatically, but its control can be interrupted by the system operator at any time and restarted from the previously stopped condition or reformatted if necessary.

Figure 3:
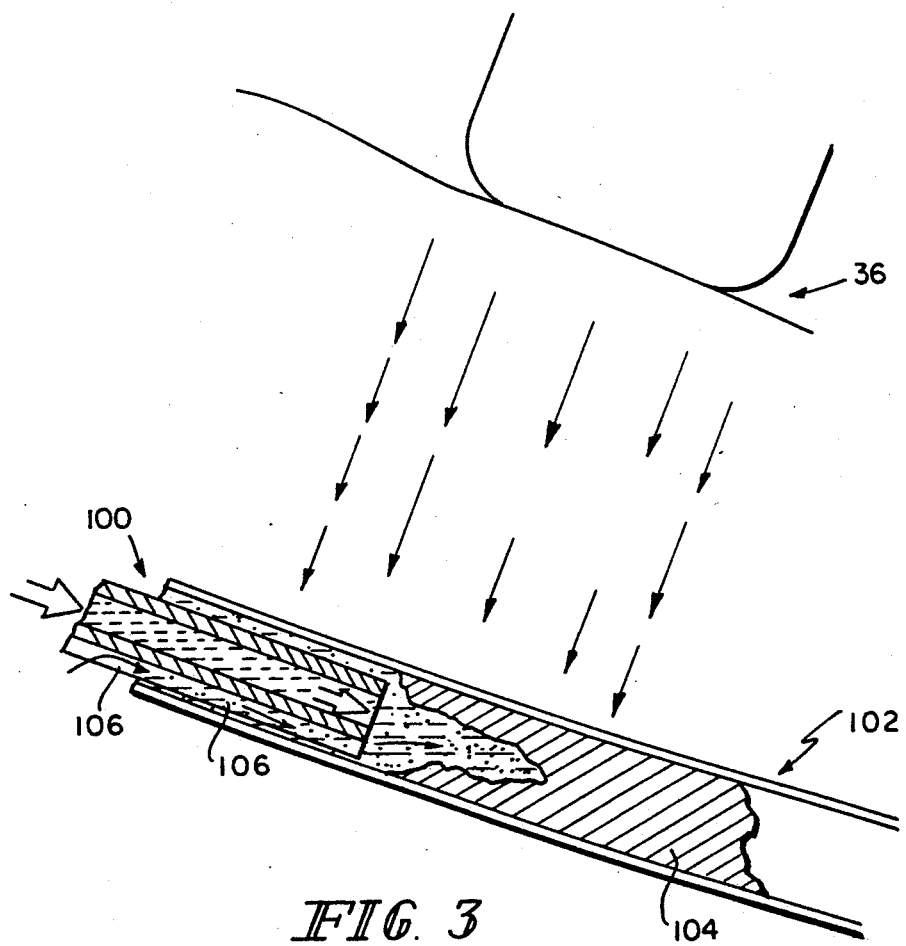
FIG. 3 illustrates a longitudinal sectional view of a portion of another apparatus for conducting the methods of the present invention.

A mechanism for intraductal or intravascular applications of chemicals is illustrated in FIG. 3. There, a flexible catheter 100 is inserted into a blood vessel 102 containing a clot 104 which is to be treated to remove it. A chemical which is a solvent for the clot 104 is supplied through catheter 100. For transcutaneous application of ultrasound to cover the clot region, transducer treatment head 36 would be positioned in accordance with the principles described in connection with the detailed discussion of FIG. 1. For intraductal application of ultrasound, the catheter 100 would either be a flexible wire guide for ultrasound applied at the outer catheter end (not shown) outside the duct, or would have a small transducer (not shown) at the catheter tip which would be electrically driven from outside by an external power supply such as power source 94 illustrated in FIG. 1. A side port or longitudinal slot 106 is illustrated to permit some blood to flow in the vessel 102 as clot 104 is being dissolved.

Successful use of the technique of the present invention requires that the combination of chemicals and ultrasound be no more traumatic, and preferably be substantially less traumatic, than existing surgical methods. To achieve this goal, both the chemicals and the ultrasound must meet the above objective. The ultrasound dosage must be such that tissue-damaging hyperthermia is not produced in normal tissue surrounding the treated region. It is also generally preferred that the treated region not be subjected to hyperthermia (prolonged temperature, that is, for longer than 15-30 minutes, above about 42° C.), although this possibility is not excluded if it is a part of the combined chemical and ultrasound regimen.

In the case of the gallbladder, the ultrasound frequency, dosage and beam configuration is such that hyperthermia is not induced in the tissue surrounding the gallbladder envelope. Gallbladder extinction is achieved over a period of approximately six (6) weeks after treatment in swine studies. A typical ultrasound regimen uses an ultrasound frequency of 220 KHz, a spatial and temporal peak intensity of 18 $Wcm^{-2}$ to 24 $Wcm^{-2}$ with a half-intensity beam diameter of 3 cm to 4 cm. The sound is delivered in a pulse mode of 4 seconds on, 22 seconds off for a total elapsed time of 90 minutes. With an appropriate chemical as discussed below, human cholesterol gallstones surgically implanted into live pig gallbladders will be totally dissolved, and, over a period of 6 weeks, the gallbladder will become a small fibrotic tissue mass indicating gallbladder extinction. All of these processes are accomplished without evidence of damage to the pig as evidenced by weight, blood and pathology analyses.

Other body sacs (e.g. appendix, cysts) can be treated in a similar manner, that is, by perfusion of chemicals either by systemic administration or injection into solid tissues (e.g. neoplasm or other undesired growth) followed by treatment with ultrasound with approximately the same delivery format.

In the case of small solid masses or small sacs, it appears to be appropriate to scan a more focused ultrasound beam across the target in a manner to cover the appropriate volume rather than use the broad ultrasound beam format approach indicated above.

For intraductile or intravascular disease, the chemical would be delivered systemically or intraductally and the ultrasound delivered extra- or intraductally by an appropriate ultrasound source. If the ultrasound is delivered intraductally, the ultrasound transducer will be mounted on an appropriate catheter, as noted in the discussion of FIG. 3.

In the gallbladder, chemicals are known which, when used with transcutaneously applied ultrasound, will rapidly dissolve cholesterol gallstones. Two such chemicals are monooctanoin and methyl-tert-butyl ether (MTBE). It now appears that MTBE when used in combination with the appropriate ultrasound regimes, can also extinguish the gallbladder. Although it may not be possible completely to separate gallstone dissolution alone from combined gallstone dissolution/gallbladder ablation, it appears that gallstone dissolution alone without gallbladder ablation can be achieved in 96% of cholelithiasis cases, while gallstone dissolution with gallbladder ablation appears capable of achievement in 95% of cases in which cholecystectomy is indicated. The availability of specific treatments to specific patients is primarily a matter of clinical judgment.

As a general rule, the chemicals appropriate for a specific therapy are those which are known to produce at least some therapeutic effect, which then is greatly enhanced by the application of ultrasound in the appropriate delivery format.

A first control group of three pigs (Pigs 1–3 in Table I) had human gallstones surgically implanted in their gallbladders. These pigs received 7 $cm^3$ methyl-tert-butyl ether (MTBE) bolus every thirty minutes. At the beginning of each MTBE treatment, 7 $cm^3$ of fluid is withdrawn from the gallbladder. A second control group of nine pigs (Pigs 4–12 in Table I) had human gallstones surgically implanted in their gallbladders. These pigs received 7 $cm^3$ MTBE bolus every ten minutes. As before, at the beginning of each MTBE treatment, 7 $cm^3$ of fluid is withdrawn from the gallbladder. A group of ten experimental pigs (Pigs 13–22 in Table II) had human gallstones surgically implanted in their gallbladders. These pigs received 7 $cm^3$ MTBE bolus every ten minutes. The ten experimental pigs received an ultrasound exposure treatment combined with their MTBE treatment. The ultrasound parameters used were: a frequency of 219 KHz; a spatial peak-temporal peak (SPTP) intensity of 15 to 21 $W/cm^2$ beam cross sectional area through the region of the gallbladder; a duty cycle of 4 seconds on /22 seconds off; and a total ultrasound exposure time of 15 minutes for a total treatment time of 1 hour, 37.5 minutes.

MTBE was administered to all pigs via catheter directly into their gallbladders. At the end of each treatment, the MTBE was evacuated from each animal's gallbladder, and the gallbladder was flushed with sterile Ringer's solution.

Blood samples were drawn from all animals before treatment began, after treatment was completed, and then at one week intervals until sacrifice. Blood analyses included SMAC 24 for indicators of liver

TABLE I

In Vivo Control Group
*MTBE infusion only*

| Pig # | # of stones implanted | total Mass of stones (g) | *survival time (wks) | absolute stone reduction (g) | % mass loss |
|---|---|---|---|---|---|
| 1 | 3 | 0.512 g | 2 wks | 0.181 g | 35.3% |
| 2 | 4 | 0.529 g | 4 wks | 0.171 g | 32.3% |
| 3 | 2 | 0.520 g | 6 wks | 0.037 g | 7.1% |
| 4 | 3 | 0.501 g | 0 wk | 0.038 g | 7.6% |
| 5 | 2 | 0.537 g | 0 wk | 0.183 g | 34.0% |
| 6 | 2 | 0.549 g | 0 wk | 0.372 g | 67.6% |
| 7 | 4 | 0.514 g | 2 wks | 0.322 g | 62.6% |
| 8 | 1 | 0.505 g | 2 wks | 0.189 g | 37.4% |
| 9 | 2 | 0.505 g | 4 wks | 0.457 g | 90.5% |
| 10 | 3 | 0.543 g | 4 wks | 0.321 g | 59.1% |
| 11 | 2 | 0.549 g | 6 wks | 0.372 g | 67.8% |
| 12 | 2 | 0.502 g | 6 wks | 0.198 g | 39.4% |

Pigs 1-3 were infused with a 7 $cm^3$ bolus of MTBE every 30 minutes. Pigs 4-12 were infused with a 7 $cm^3$ bolus of MTBE every 10 minutes.
Pigs 1-12 - Average ± 1.0 standard deviation for various parameters of interest:
Pigs 1-12, No of stone implanted - 2.5 ± 0.9
Pigs 1-12, total mass of stones - 30 min. infusion: 0.5203 ± 0.0085 g 10 min. infusion: 0.5228 ± 0.0212 g total: 0.5221 ± 0.0185 g
Pigs 1-12, absolute stone reduction - 30 min. infusion: 0.1297 ± 0.0804 g 10 min. infusion: 0.2724 ± 0.1295 g total: 0.2368 ± 0.1324 g
Pigs 1-12, percentage stone mass loss - 30 min. infusion: 24.90 ± 15.49% 10 min. infusion: 57.78 ± 24.50% total: 45.06 ± 25.06%

TABLE II

In Vivo Treatment Group
*MTBE and ultrasound*

| Pig # | # of stones implanted | total mass of stones (g) | +recovery time (wks) | *survival time (wks) | absolute stone reduction (g) | % mass loss |
|---|---|---|---|---|---|---|
| 13 | 4 | 0.495 g | 8 wks | 2 wks | 0.495 g | 100% |
| 14 | 3 | 0.502 g | 4 wks | 2 wks | 0.502 g | 100% |

TABLE II-continued

In Vivo Treatment Group
*MTBE and ultrasound*

| Pig # | # of stones implanted | total mass of stones (g) | +recovery time (wks) | *survival time (wks) | absolute stone reduction (g) | % mass loss |
|---|---|---|---|---|---|---|
| 15 | 5 | 0.524 g | 3 wks | 2 wks | 0.380 g | 72.5% |
| 16 | 1 | 0.513 g | 3 wks | 1 wk | 0.400 g | 78.0% |
| 17 | 2 | 0.551 g | 1 wk | 4 wks | 0.551 g | 100% |
| 18 | 3 | 0.505 g | 8 wks | 4 wks | 0.497 g | 98.4% |
| 19 | 8 | 0.514 g | 2 wks | 4 wks | 0.514 g | 100% |
| 20 | 7 | 0.491 g | 9 wks | 6 wks | 0.491 g | 100% |
| 21 | 2 | 0.506 g | 6 wks | 6 wks | 0.356 g | 70.4% |
| 22 | 2 | 0.502 g | 5 wks | 6 wks | 0.502 g | 100% |

Averages ± 1.0 standard deviation for various parameters of interest
Pigs 13–22, No. of stone implanted - 3.7 ± 2.3
Pigs 13–22, total mass of stones - 0.510 g ± 0.017 g
Pigs 13–22, absolute stone reduction - 0.469 g ± 0.065 g
Pigs 13–22, percentage stone mass loss - 91.9 ± 12.8%
+Recovery time is the number of weeks from the surgical implant of the stone(s) to treatment
*Survival time is the number of weeks from treatment to sacrifice dysfunction (SGPT, SGOT, LDH, alkaline phosphatase, total bilirubin, cholesterol and A/G ratio). At autopsy, tissue samples were obtained from the gallbladder, liver, irradiated overlying abdominal muscle and skin, irradiated region of the bowel, and so on. These samples were examined for edema, coagulative changes, acute inflammation, chronic inflammation and fibrosis. A pathologist scored each sample on a scale of zero to five with five being the greatest amount of edema, coagulative changes, and so on. Tables III, IV and V illustrate the pathology scoring for gallbladder, liver and skin/abdominal wall, respectively.

The changes to stone mass among the control pigs 1–12 are illustrated in Table I. The average absolute reduction in stone mass among control pigs 4–12 (those given MTBE every ten minutes) was 0.2368 gram±0.1324 gram (57.78% of original mass±24.5% of original mass). The changes in stone mass among the test pigs 13–22 are illustrated in Table II. The absolute reduction in stone mass among the ten experimental pigs 13–22 was 0.469 gram±0.065 gram (91.9% of original mass±12.8% of original mass).

The pathology scoring for livers demonstrated no observable effect. Therefore the results were not analyzed statistically. The pathology scoring for the gallbladder was analyzed separately using two-way analysis of variance. The two-way analysis of variance for each pathological appearance considered both treatment (MTBE only versus MTBE plus ultrasound exposure) and survival time (2, 4 or 6 weeks) as

TABLE III

Pathology Scores* for Gallbladder

| | | | | Pathological appearance | | |
|---|---|---|---|---|---|---|
| | | survival | | coagulative | inflammation | |
| pig | conditions | time | edema | changes | acute | chronic | fibrosis |
| 1 | MTBE only** | 2 wks | 0 | 0 | 0 | 2+ | 0 |
| 7 | MTBE only*** | 2 wks | 0 | 0 | 0 | 1–2+ | 1+ |
| 13 | MTBE + US | 2 wks | 0 | 0 | 1+ | 1–2+ | 2–3+ |
| 14 | MTBE + US | 2 wks | 0 | 4+ | 2–3+ | 2+ | 4+ |
| 15 | MTBE + US | 2 wks | +/− | — | — | 1–2+ | 1+ |
| 2 | MTBE only** | 4 wks | 0 | 0 | 0 | +/− | 1+ |
| 9 | MTBE only*** | 4 wks | 0 | 0 | 0 | 0 | 0 |
| 17 | MTBE + US | 4 wks | — | — | 1+ | 4+ | 3–4+ |
| 18 | MTBE + US | 4 wks | 0 | — | 0 | 1–2+ | 3+ |
| 19 | MTBE + US | 4 wks | 0 | 0 | 0 | 2–3+ | 3–4+ |
| 3 | MTBE only** | 6 wks | 0 | 0 | 0 | 0 | 0 |
| 11 | MTBE only*** | 6 wks | 0 | 0 | 1+ | 0 | 0 |
| 20 | MTBE + US | 6 wks | 0 | 0 | 0 | 2–3+ | 3–4+ |
| 21 | MTBE + US | 6 wks | 0 | 0 | 1+ | 4+ | 4+ |
| 22 | MTBE + US | 6 wks | 0 | 0 | +/− | 3–4+ | 4+ |

*scored on a scale of 0 to 5, with 5 being the highest
**methyl tert-butyl ether infusion rate was 7 cc bolus/30 minutes
***methyl tert-butyl ether infusion rate was 7 cc bolus/10 minutes

TABLE IV

Pathology Scores* for Liver

| | | | | Pathological appearance | | |
|---|---|---|---|---|---|---|
| | | survival | | coagulative | inflammation | |
| pig | conditions | time | edema | changes | acute | chronic | fibrosis |
| 1 | MTBE only** | 2 wks | 0 | 0 | 0 | 0 | 0 |
| 7 | MTBE only*** | 2 wks | 0 | 0 | 0 | 0 | 0 |
| 13 | MTBE + US | 2 wks | 0 | 0 | 0 | 0 | 0 |
| 14 | MTBE + US | 2 wks | 0 | 0 | 0 | 0 | 0 |
| 15 | MTBE + US | 2 wks | 0 | 0 | 0 | 0 | 0 |
| 2 | MTBE only** | 4 wks | 0 | 0 | 0 | 0 | 0 |
| 9 | MTBE only*** | 4 wks | 0 | 0 | 0 | 0 | 0 |
| 17 | MTBE + US | 4 wks | 0 | 0 | 0 | 0 | 0 |

TABLE IV-continued

Pathology Scores* for Liver

| pig | conditions | survival time | Pathological appearance | | | | |
|---|---|---|---|---|---|---|---|
| | | | edema | coagulative changes | inflammation acute | inflammation chronic | fibrosis |
| 18 | MTBE + US | 4 wks | 0 | 0 | 0 | 0 | 0 |
| 19 | MTBE + US | 4 wks | 0 | 0 | 0 | 0 | 0 |
| 3 | MTBE only** | 6 wks | 0 | 0 | 0 | 0 | 0 |
| 11 | MTBE only*** | 6 wks | 0 | 0 | 0 | 0 | 0 |
| 20 | MTBE + US | 6 wks | 0 | 0 | 0 | 0 | 0 |
| 21 | MTBE + US | 6 wks | 0 | 0 | 0 | 0 | 0 |
| 22 | MTBE + US | 6 wks | 0 | 0 | 0 | 0 | 0 |

*scored on a scale of 0 to 5, with 5 being the highest
**methyl tert-butyl ether infusion rate was 7 cc bolus/30 minutes
***methyl tert-butyl ether infusion rate was 7 cc bolus/10 minutes

TABLE V

Pathology Scores* for Skin/Abdominal Wall

| pig | conditions | survival time | Pathological appearance | | | | |
|---|---|---|---|---|---|---|---|
| | | | edema | coagulative changes | inflammation acute | inflammation chronic | fibrosis |
| 1 | MTBE only** | 2 wks | — | — | — | — | — |
| 7 | MTBE only*** | 2 wks | 0 | 0 | 0 | 0 | 0 |
| 13 | MTBE + US | 2 wks | 0 | 0 | 0 | +/− | 3+ |
| 14 | MTBE + US | 2 wks | 0 | 0 | 0 | 0 | 3+ |
| 15 | MTBE + US | 2 wks | 0 | 0 | 1+ | 0 | 3-4+ |
| 2 | MTBE only** | 4 wks | — | — | — | — | — |
| 9 | MTBE only*** | 4 wks | — | — | — | — | — |
| 17 | MTBE + US | 4 wks | 0 | 0 | 0 | 0 | 0 |
| 18 | MTBE + US | 4 wks | 0 | 0 | 0 | 1+ | 3+ |
| 19 | MTBE + US | 4 wks | 0 | 0 | 0 | 0 | 0 |
| 3 | MTBE only** | 6 wks | — | — | — | — | — |
| 11 | MTBE only*** | 6 wks | — | — | — | — | — |
| 20 | MTBE + US | 6 wks | 0 | 0 | 0 | 0 | 0 |
| 21 | MTBE + US | 6 wks | — | — | — | — | — |
| 22 | MTBE + US | 6 wks | — | — | — | — | — |

*scored on a scale of 0 to 5, with 5 being the highest
**methyl tert-butyl ether infusion rate was 7 cc bolus/30 minutes
***methyl tert-butyl ether infusion rate was 7 cc bolus/10 minutes independent factors. Significant differences ($p<0.10$) were detected in the gallbladder for acute inflammation, chronic inflammation and fibrosis. In considering acute inflammation, a significant difference ($p=0.094$) was noted between the two treatments. For chronic inflammation, a significant interaction ($p=0.030$) was detected between treatment and survival time. This interaction is a result of the two groups having similar mean scores at two weeks but not at the later survival times. The MTBE plus ultrasound test group had higher mean scores than the MTBE alone group at both four and six weeks. Finally fibrosis scores were significantly higher ($p=0.0003$) for the MTBE plus ultrasound test group than for the MTBE alone group.

The pathology of the gallbladder reveals that the MTBE plus ultrasound treatment regime not only has the effect of dissolving the gallstones, but also of significantly dysfunctionalizing the gallbladder itself. The gallbladder became a fibrotic tissue mass with either an extremely small lumen or no lumen. This means that gallstones could not recur in these animals. The pigs 13-22 subjected to the experimental treatment suffered no adverse effects in their eating habits, gastrointestinal function, weight gain or any of the other parameters monitored during the study. The control pigs 1-12 did not show this gallbladder dysfunctionalization.

In another set of trials, two pigs had human gallstones surgically implanted in their gallbladders. These two pigs, along with a third control pig with no surgically implanted human gallstones, had their gallbladders irradiated with ultrasound in a delivery format of: 236 KHz ultrasound irradiation frequency; SPTP intensity 18-21 $W/cm^2$ beam cross sectional area through the region of the gallbladder; a duty cycle of four seconds on/twenty-two seconds off; and a total elapsed time of 3.25 hours for a total ultrasound exposure time of thirty minutes. Pretreatment and post-treatment blood enzyme analyses, observation of gross tissue effects at autopsy, and pathology examination with scoring for edema, coagulative changes, inflammation and fibrosis were conducted.

The blood enzyme analyses are presented in Table VI.

TABLE VI

| Enzyme | Pre-treatment | Post-Treatment |
|---|---|---|
| alkaline phosphatase | 235 U/l | 268 U/l |
| LDH | 581 U/l | 490 U/l |
| SGOT | 55 U/l | 49 U/l |
| SGPT | 82 U/l | 84 U/l |
| A/G ratio | 1.2 | 1.1 |

Gross observation of the control pig at autopsy revealed a reddish area, believed to be a superficial burn, on the pig's skin about 2.5 cm to 3.0 cm in diameter at the point of ultrasound entry. No irregularities were noticed on inspection of this pig's abdominal muscular tissue, liver or gallbladder. Pathology confirmed these gross observations.

The two pigs with implanted human stones which had been ultrasonically irradiated were both sacrificed at four weeks after treatment. Of these two pigs with implanted human gallstones exposed to ultrasound treatments, the losses in masses of the implanted stones were 145 mg of an initial mass of 502 mg (four stones—28.9% of the initial mass) and 269 mg of an initial mass of 516 mg (three stones—52.1% of the initial mass). Gross observation of these two pigs did not reveal any remarkable alterations other than the reduction in implanted stone mass. Specifically, there was no edema or other apparent harm to the gallbladder or cystic duct. These trials demonstrate a remarkable reduction in the masses of gallstones is achievable by the application of ultrasound alone in the appropriate format.

What is claimed is:

1. A method for rendering a gallbladder dysfunctional without surgical removal comprising the steps of infusing the gallbladder with methyl-tert-butyl ether (MTBE), then, while the gallbladder is so infused, irradiating the gallbladder with an ultrasound beam in such an ultrasound delivery format as not to elevate the average temperature of the gallbladder more than five degrees Centigrade over the period of treatment, and then removing the MTBE from the gallbladder, and then repeating these steps a sufficient number of times to render the gallbladder dysfunctional.

2. The method of claim 1 wherein the steps of infusing the gallbladder with MTBE and then removing the MTBE from the gallbladder comprise the steps of placing a catheter into the gallbladder, periodically administering MTBE bolus into the gallbladder, and periodically removing the MTBE from the gallbladder.

3. The method of claim 1 and further comprising the step of flushing the gallbladder with a sterile fluid after the step of removing the MTBE from the gallbladder.

4. The method of 1 wherein the ultrasound delivery format includes a frequency in the range of 200–250 KHz, a spatial peak-temporal peak (SPTP) intensity of 12–24 $W/cm^2$ over the cross sectional area of the gallbladder, a duty cycle in the range of 10%–20%, and an ultrasound exposure time of 30–90 minutes.

* * * * *